US005583339A

United States Patent [19]

Black et al.

[11] Patent Number: 5,583,339
[45] Date of Patent: Dec. 10, 1996

[54] INFRARED METHOD AND APPARATUS FOR MEASURING GAS CONCENTRATION OF A PLURALITY OF COMPONENT GASES IN A SAMPLE

[75] Inventors: Karl H. Black, Dexter; Walter I. Armstrong, Saline, both of Mich.

[73] Assignee: Sensors, Inc., Saline, Mich.

[21] Appl. No.: 433,078

[22] Filed: May 3, 1995

Related U.S. Application Data

[62] Division of Ser. No. 212,264, Mar. 14, 1994, Pat. No. 5,510,269, Continuation-in-part of Ser. No. 979,818, Nov. 20, 1992, abandoned.

[51] Int. Cl.[6] ............................................. G01N 21/61
[52] U.S. Cl. ................................. 250/339.13; 250/343
[58] Field of Search ........................... 250/339.13, 343, 250/341.7, 495.1

[56] References Cited

U.S. PATENT DOCUMENTS

| | | | |
|---|---|---|---|
| 2,718,597 | 9/1955 | Heigl et al. | |
| 3,790,797 | 2/1974 | Sternberg et al. | 250/345 |
| 3,860,344 | 1/1975 | Garfunkel | 250/339.13 |
| 3,860,818 | 1/1975 | Stalder et al. | 250/343 |
| 3,861,809 | 1/1975 | Hall, Jr. | 250/343 |
| 3,887,473 | 6/1975 | Sternberg et al. | 250/345 |
| 3,898,462 | 8/1975 | Ishida et al. | 250/344 |
| 3,923,403 | 12/1975 | Harklau | 250/559 |
| 4,011,859 | 3/1977 | Frankenberger | |
| 4,042,333 | 8/1977 | Dell et al. | 356/246 |
| 4,050,823 | 9/1977 | Frankenberger | 250/343 |
| 4,069,420 | 1/1978 | Ross | 250/343 |
| 4,075,481 | 2/1978 | Stoft et al. | 250/343 |
| 4,126,396 | 11/1978 | Hartmann et al. | 250/373 |
| 4,167,665 | 7/1979 | Johns et al. | 250/573 |
| 4,346,296 | 8/1982 | Passaro et al. | 250/343 |
| 4,348,115 | 9/1982 | Walker et al. | 356/436 |
| 4,358,679 | 11/1982 | Lipoma | 250/343 |
| 4,370,553 | 1/1983 | Waycaster et al. | 250/343 |

(List continued on next page.)

FOREIGN PATENT DOCUMENTS

| | | |
|---|---|---|
| 159366 | 3/1983 | Germany . |
| 2031146 | 4/1980 | United Kingdom . |
| 2215038 | 9/1989 | United Kingdom . |
| WO8604411 | 7/1986 | WIPO . |
| WO8606638 | 11/1986 | WIPO . |
| WO8903028 | 4/1989 | WIPO . |

OTHER PUBLICATIONS

European Search Report for Application No. EP 93 30 9170.
Jones, T. A.; Firth, J. G.; and Jones, A., "A Simple Infrared Gas Analyzer," *Journal of Physics E: Scientific–Instruments*, vol. 4, pp. 792 and 793, 1971.
Johnston, Sean F., "Gas Monitors Employing Infrared LEDs," *Meas. Sci. Technol.*, No. 2, pp. 191–195, Feb., 1992.
Mindock, Ralph M. and Allen, David M., "Miniature NDIR Gas Sensors," *ISA Proceedings*, vol. 43, pp. 1071–1081, 1988.

*Primary Examiner*—Carolyn E. Fields
*Attorney, Agent, or Firm*—Van Dyke, Gardner, Linn & Burkhart, LLP

[57] ABSTRACT

An automatic calibration technique for a gas analyzer includes applying electrical energy to a source that is different from the level used to detect gas concentration in order to produce a different level of radiation from that used to detect gas concentration. The reduced level is applied with a non-absorbing gas in the gas sample chamber. The detector output at the reduced level is resolved to a calibration factor. The instrument can be linearized by repeating the calibration procedure at multiple different levels of reduced source radiation. In one embodiment, a source assembly is provided that includes a plurality of infrared emitters to which is applied modulated electrical energy in a timed sequence in order to produce output levels for three component gas concentrations. A filter between each one of the sources and a detector pass radiation at an absorption line of one of the component gases.

7 Claims, 8 Drawing Sheets

U.S. PATENT DOCUMENTS

| | | | |
|---|---|---|---|
| 4,381,153 | 4/1983 | Bohl et al. | 356/437 |
| 4,423,739 | 1/1984 | Passaro et al. | 250/343 |
| 4,480,190 | 10/1984 | Burough et al. | 250/343 |
| 4,620,104 | 10/1986 | Nordal et al. | 250/495.1 |
| 4,673,812 | 6/1987 | Yoneda | 250/252.1 A |
| 4,678,914 | 7/1987 | Melrose et al. | 250/343 |
| 4,687,934 | 8/1987 | Passaro et al. | 250/343 |
| 4,694,173 | 9/1987 | Wong | 250/343 |
| 4,730,112 | 3/1988 | Wong | 250/343 |
| 4,756,622 | 7/1988 | Wong | 356/437 |
| 4,787,750 | 11/1988 | Nelson et al. | 356/437 |
| 4,794,258 | 12/1988 | Fetzer et al. | 250/343 |
| 4,795,240 | 1/1989 | Wong et al. | |
| 4,914,719 | 4/1990 | Conlon et al. | 250/343 |
| 5,013,920 | 5/1991 | Asano et al. | 250/343 |
| 5,039,855 | 8/1991 | Kemeny et al. | 250/343 |
| 5,060,505 | 10/1991 | Tury et al. | 250/343 |
| 5,134,302 | 7/1992 | Rosenthal | 250/495.1 |
| 5,160,843 | 11/1992 | Lehto | 250/343 |
| 5,401,966 | 3/1995 | Gray et al. | 250/339.13 |

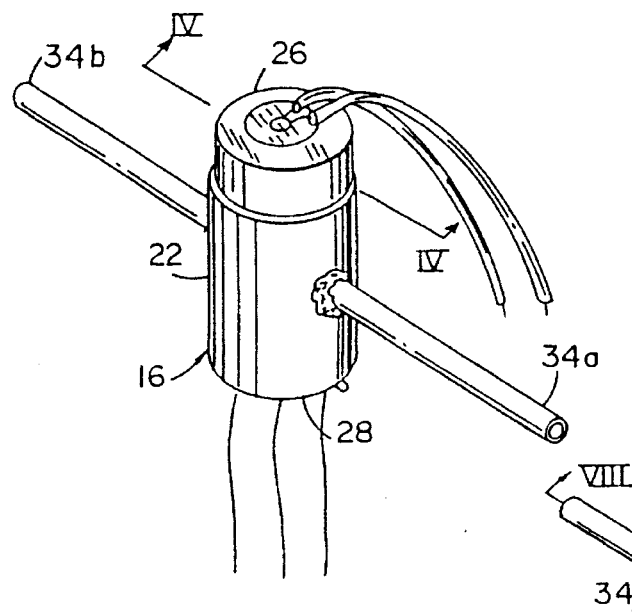
FIG. 2
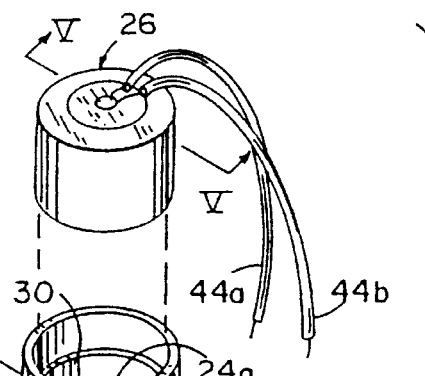
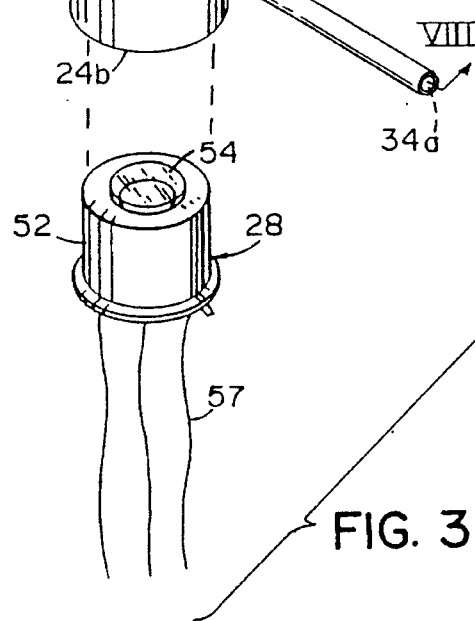
FIG. 3
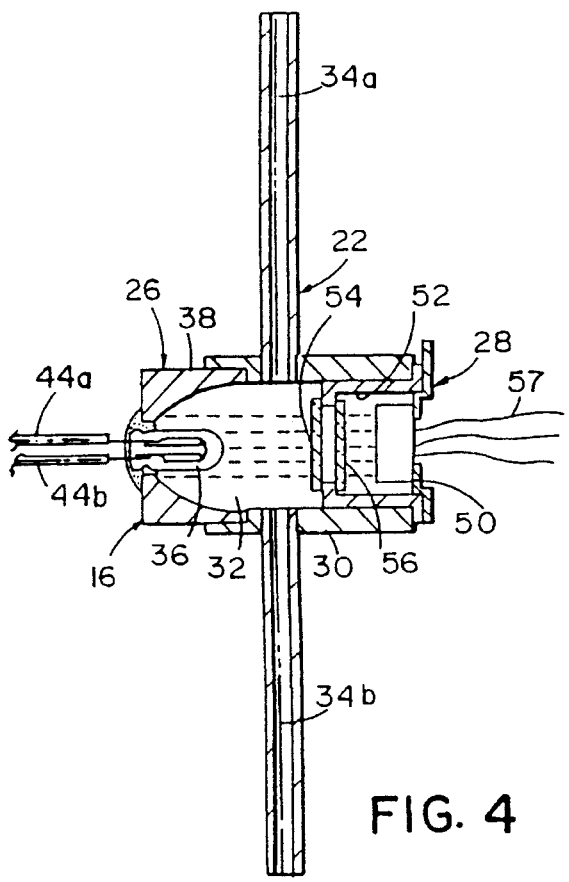
FIG. 4

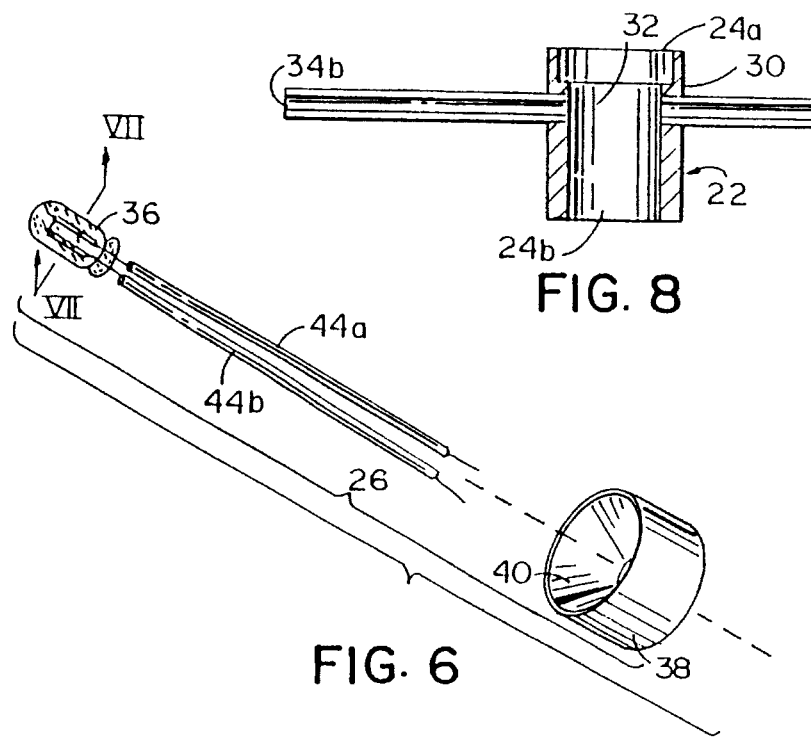
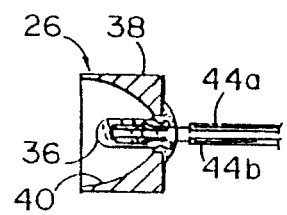
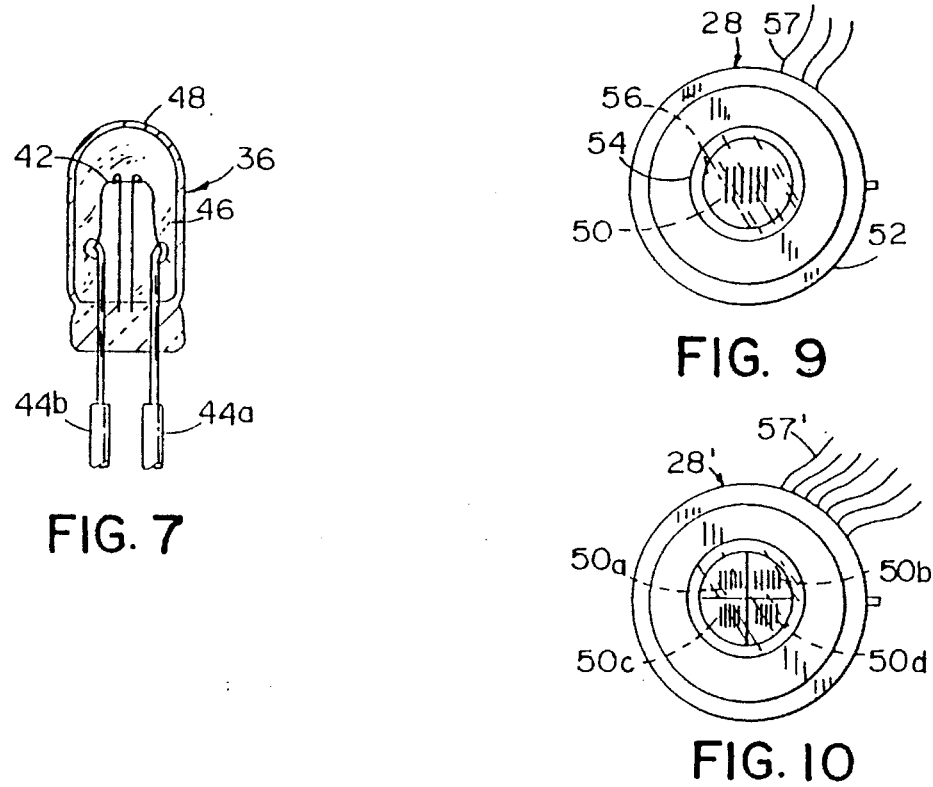

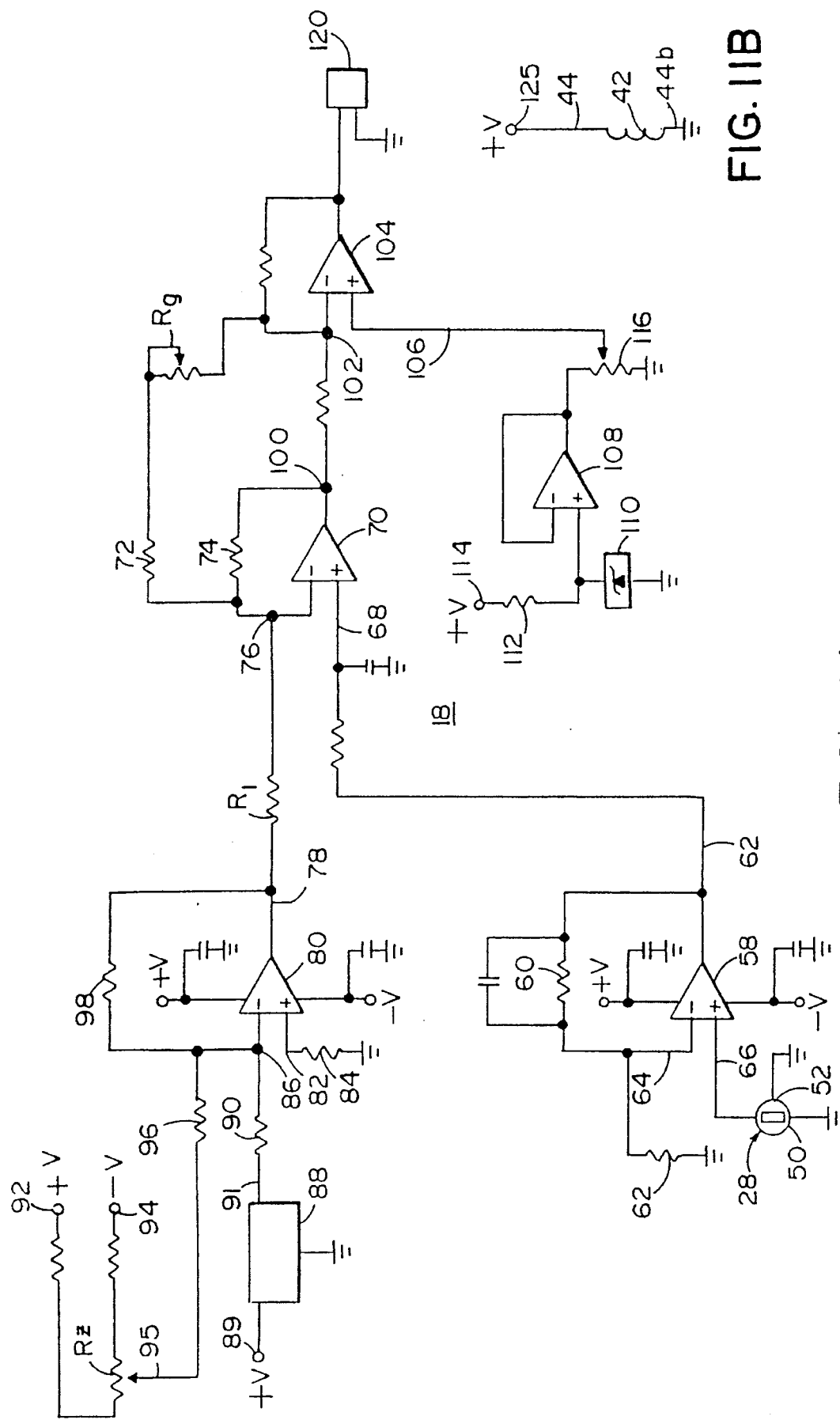

INFRARED METHOD AND APPARATUS FOR MEASURING GAS CONCENTRATION OF A PLURALITY OF COMPONENT GASES IN A SAMPLE

CROSS-REFERENCE TO RELATED APPLICATIONS

This application is a division of application Ser. No. 08/212,264, filed Mar. 14, 1994, now U.S. Pat. No. 5,510,269, issued Apr. 23, 1996, which is a continuation-in-part of application Ser. No. 07/979,818, filed Nov. 20, 1992, now abandoned.

BACKGROUND OF THE INVENTION

This invention relates generally to gas analyzers for detecting one or more component gas concentrations in a sample and, more particularly, to non-dispersive infrared gas analyzers.

Non-dispersive infrared gas analyzers have long been known. Such analyzers direct a source of infrared radiation along an optical path in a preselected spectral band having at least one absorption line of the component gas to be detected. A detector, positioned in the optical path, detects radiation in the preselected spectral band and produces a detector output. A sample chamber is positioned in the optical path between the source and the detector in order to contain a quantity of the sample gas, which includes the component gas to be detected. Such infrared gas analyzers have suffered from numerous problems. Their response time, being on the order of one to three seconds, is much too slow for many applications. For example, it is not practical to accurately track a patient's respiration carbon dioxide level with an instrument having a response time of between one and three seconds. Furthermore, known systems have been plagued with temperature and age drift problems, which has resulted in costly and complicated compensation schemes. Such compensation schemes further limit the adaptability of the instrument because they increase the size and reduce the reliability of the instrument.

Sources for infrared gas analyzers radiate electromagnetic energy in the infrared band by applying a current to a resistance element, such as a tungsten alloy filament. In order to increase the emissivity of the source, it is known to run the source at ever-increasing temperatures. One difficulty with such an approach is that it increases the oxidation of the source element. Such oxidation not only reduces the efficiency of the source, but results in a significant amount of drift in the source emissivity over time. This instability must be compensated for in order to avoid a resulting inaccuracy in analyzer readings. One approach at solving this problem has been to coat the element with a ceramic jacket in order to avoid oxidation of the elements. Although this approach may reduce oxidation of the element per se, various oxides are still formed and deposited on the ceramic layer resulting in undesirable variation in the source emissivity.

In order to overcome the degrading effects of source oxidation on analyzer accuracy, the prior art has attempted to sense the level of source emissivity by placing, for example, temperature sensors in a position to monitor the temperature of the source. Because source emissivity is proportional to temperature, the output of the temperature sensor may be used in a feedback loop to regulate the current applied to the source and, in theory, maintain a constant level of emissivity of the source. The principle behind this approach is that, if source emissivity is regulated to a constant level, system drift will then be kept to a minimum. In practice, this has not worked satisfactorily. The extensive amount of heat generated by the source introduces second and third order errors in the detector circuitry, as well as in the system's optics. These errors have proven to be significant in degrading system performance. An alternative approach has been to apply the output of the source temperature sensor to regulate the detector circuitry. This has proven to be equally futile for the same reasons. The heating of the system components by the source has introduced errors that may not be readily compensated for.

Another approach at applying compensation to a gas analyzer system has been to divide the radiation path either spatially into two beams, a reference beam and a sensing beam, or, temporally, into a sequence of intermittent transmissions between the source and detector separated by blank periods when no beam is being transmitted. The principle behind this approach is that the detection circuitry may provide an accurate reading by comparing the reference beam, or period, with the sensed beam, or period, in order to subtract the effect of source strength from the detected signals. One approach at temporally dividing the detected signal into intermittent pulses is by chopping the light source utilizing a mechanical vibrating device or rotating device. This approach has several difficulties. The requirement for a mechanical device not only adds to the bulk and complexity of the system, but also adds to the system's low reliability. Furthermore, the thermopile detectors that are commonly used in infrared gas analyzers respond very slowly to the large swing in the detected beam between the blank periods and the sensing periods. This contributes to a system response time on the order of one to three seconds for such systems.

Another approach to temporally dividing the beam into intermittent segments is by switching the source periodically between off and on conditions. Because source emissivity is a function of heat output, they are not readily switched between off and on conditions because the heat must dissipate between each interval. As a result, switched source gas analyzers have the same difficulty of slow system response time as do the mechanically chopped beam systems. Furthermore, the periodic switching of the source introduces temperature variations to the system components, which not only degrades the system's longevity but also make appropriate compensation impractical.

In order to calibrate an infrared gas analyzer, both zero, or offset, and span calibration procedures are performed. The zero calibration is in order to compensate for any offset in the amplifiers and is traditionally performed by filling the sample chamber with a gas, such as air or nitrogen, that does not absorb infrared radiation at the absorption line of the gas detected by the analyzer. With the non-absorbing gas filling the chamber, the offset of the output is measured and, either stored for compensation in the gas concentration reading, or is reduced to a zero value. The span calibration is traditionally performed by filling the sample chamber with a known concentration of the gas or gases to be detected. The output is adjusted to correspond with the known gas concentration. Such span calibration is time-consuming and utilizes expensive calibration gases which are often toxic. As a result, alternate span calibration techniques have been proposed but all suffer from some deficiencies. One known alternative technique is to partially occlude the source with a partial transmission filter, or the like, in order to simulate the introduction of a known concentration of the gas to be measured. However, the introduction of the occluding member requires a mechanical movement.

Another alternative proposal is to inject an electrical current into the output amplifier of the electronic control in order to simulate the effect of a calibration gas in the sample chamber. While such technique does not suffer the drawbacks described with respect to the other known span calibration techniques, it is only capable of calibrating the output amplifier. It is incapable of compensating for fouling of the surfaces of the sample chamber or degradation in source performance.

In addition to the zero and the span calibrations, both of which can be performed in the field, an additional procedure must be occasionally performed at the factory or a service center. This additional procedure is a relinearization of the instrument. This results from the degradation of the source and the fouling of the sample chamber, in addition to drift and the like in the electronics, due to component aging. Because the relationship between the detector output and the source input varies according to a non-linear relationship, any variations in the performance of the component require that the instrument be calibrated at multiple values of sample gas calibration. The necessity to periodically return the instrument to the factory or a service center results in a significant increase in the total operating expense of an infrared gas analyzer.

SUMMARY OF THE INVENTION

The present invention is intended to provide a gas analyzer having a response time never before achieved in the art. This is accomplished in a manner that reduces power requirements to a level which allows operation of the gas analyzer from portable power sources, such as miniature batteries. This combination of features allows applications never before achieved with conventional gas analyzer technology. For example, response times sufficiently fast to allow real time monitoring of the carbon dioxide level of a patient's respiration are now possible. With increased reliability and superior drift performance characteristics, gas analyzer technology may be incorporated into portable diagnostic instruments as an ancillary feature to standard diagnostic tools.

The invention is embodied in an infrared gas analyzer and method for detecting a component gas in a gas sample. Infrared radiation is produced by an infrared radiation source, having at least one absorption line of a component gas to be detected, and directed along an optical path through a gas sample. A detector positioned in the optical path detects the infrared radiation attenuated by absorption of the component gas. A control resolves the detected infrared radiation to component gas concentration. The control does this in a manner that is independent of a reference level of the radiation. By avoiding the necessity for developing a reference level, the invention provides an exceptionally fast and compact apparatus with no moving parts. Response times of 250 milliseconds or less are possible according to the invention.

This may be accomplished, according to another aspect of the invention, by providing a source which includes an infrared emitter enclosed in a space defined within a gas-impervious envelope with the space being void of reactive gases. The envelope is made of a material that transmits infrared radiation. In a preferred embodiment, the space is evacuated. The material making up the envelope is quartz. In a most preferred embodiment, the source is a visible light source that is operated at approximately 50% of rated voltage. Such source is exceptionally stable and does not significantly heat the sample chamber and thereby avoids instability requiring a reference level. In addition, the source is optically coupled with the sample chamber in a manner that does not reflect heat back toward the source which causes heating in prior art units. In an illustrated embodiment, the source is in direct contact with the sample gas.

The invention provides an exceptionally compact, low power, gas analyzer which has no moving parts. The illustrated embodiment is of a gas analyzer which is capable of operation with less than one watt of power. The internal volume of the sample chamber is approximately 0.5 mm$^3$ in order to detect carbon dioxide at 0–20% concentrations. The entire gas analyzer occupies a volume of less than two cubic inches. The invention may be adapted to detecting multiple component gases in a sample in a manner which is set forth in detail in the following specification.

According to another aspect of the invention, a calibration technique for a gas analyzer is provided. The technique includes applying electrical energy to the source at a level that is different from the level used to detect gas concentration in order to produce a different level of radiation from that used to detect gas concentration. This different level of radiation is directed through an optical path other than through the gas sample in order to produce a detector output value. The detector output is resolved to a calibration factor. This aspect of the invention requires a source and detector that are characterized by a linear relationship between energy applied to the source and the output signal derived from the detector. In this manner, a known reduction in the energy applied to the source results in a proportionate reduction in the anticipated detector output. By comparing the anticipated detector output for a given source energy level with the measured detector output, a calibration factor may be stored in a look-up table and applied to the actual detector output during sample gas measurement procedures.

A calibration technique according to the invention additionally comprehends an improved linearization of the instrument that is performed by repeating the span calibration at multiple different levels of source radiation. Not only does such procedure avoid the use of expensive and often toxic calibration gases, or mechanical components to impose a shutter in the gas pathway, it also provides for complete calibration of the entire gas analyzer including the source, sample chamber walls, and the detector. Advantageously, this is accomplished by a software procedure which may be carried out with an on-board microprocessor or other control circuitry. Advantageously, the procedure can be performed in the field and, indeed, may be performed in the amount of time that is dedicated to the zeroing of prior art instruments.

These and other objects, advantages and features of this invention will become apparent upon review of the following specification in conjunction with the drawings.

BRIEF DESCRIPTION OF THE DRAWINGS

FIG. 2 is the same view as FIG. 1 of a sensing assembly;

FIG. 3 is an exploded perspective view of the sensing assembly in FIG. 2;

FIG. 4 is a sectional view taken along the lines IV—IV in FIG. 2;

FIG. 5 is a sectional view taken along the lines V—V in FIG. 3;

FIG. 6 is an exploded perspective view of a source assembly according to the invention;

FIG. 7 is an enlarged sectional view taken along the lines VII—VII in FIG. 6;

FIG. 8 is a sectional view taken along the lines VIII—VIII in FIG. 3;

FIG. 9 is an end elevation of a detector useful with the invention;

FIG. 10 is the same view as FIG. 9 of an alternative embodiment of a detector;

FIG. 11 is an electrical schematic diagram of a circuit useful with the invention;

DESCRIPTION OF THE PREFERRED EMBODIMENT

Figure 1:
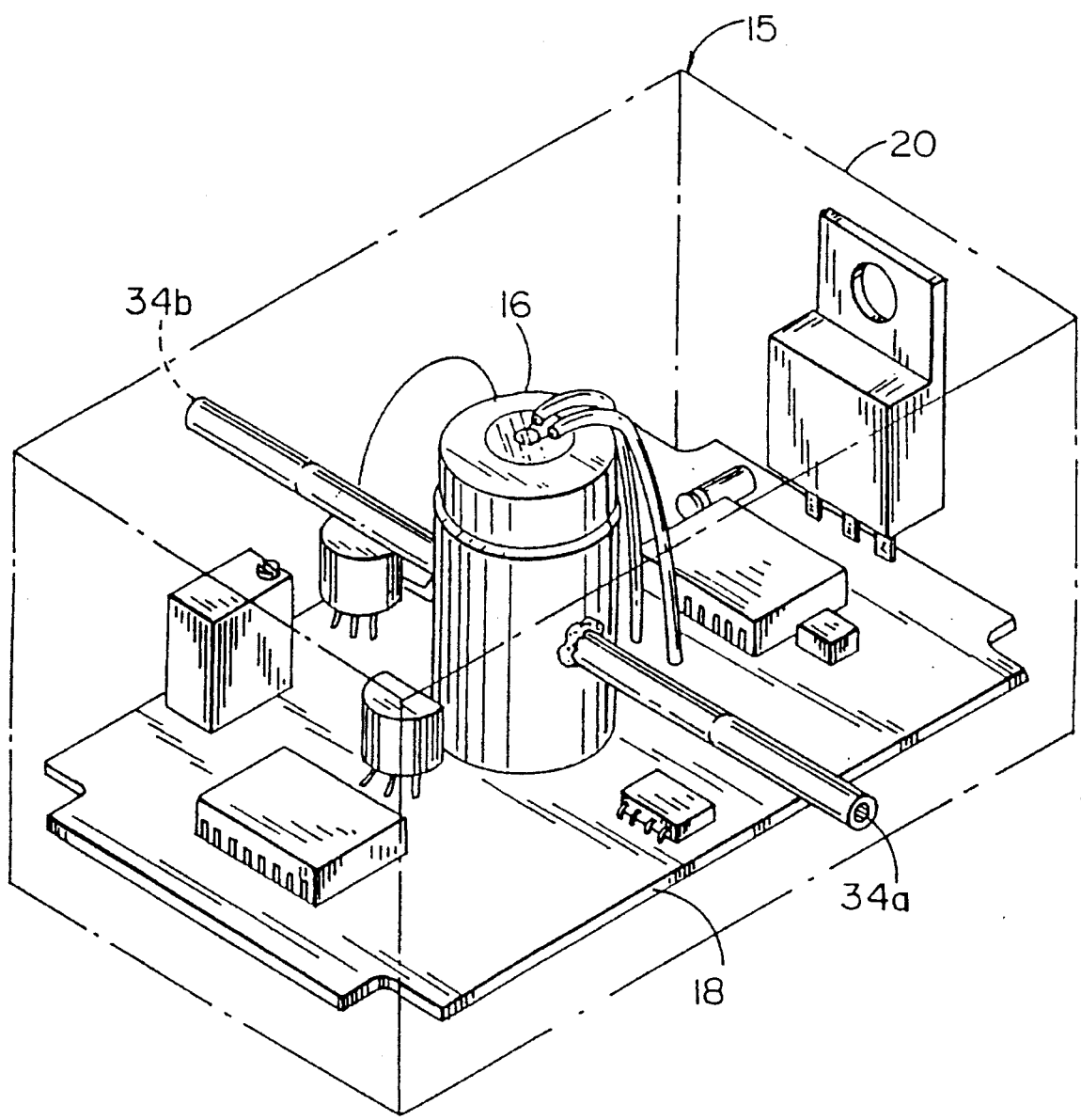
FIG. 1 is a perspective view of an infrared gas analyzer according to the invention.

Referring now specifically to the drawings, and the illustrative embodiments depicted therein, an infrared gas analyzer 15 includes a sensor assembly 16 mounted to an electronic assembly 18 and encapsulated within encapsulation material 20 (FIG. 1). A metallic jacket (not shown) encloses encapsulation material 20. In the illustrated embodiment, encapsulation material 20 is silicone rubber and is surrounded by a cast-aluminum jacket.

Sensor assembly 16 includes a tubular sample chamber assembly 22 having open ends 24a and 24b thereof, a source assembly 26 fitted within one open end 24a and a detector assembly 28 fitted within the other open end 24b (FIGS. 2–4). Sample chamber assembly 22 includes a cylindrical wall 30 which, along with source assembly 26 and detector assembly 18, encloses a sample chamber 32. A pair of tubes 34a, 34b penetrate wall 30 in order to provide ingress and egress of a sample gas into sample chamber 32. The sample gas may be supplied to sample chamber 32 under positive pressure by a sample pump (not shown) or by diffusion. In the illustrated embodiment of a carbon dioxide ($CO_2$) gas analyzer for sensing between zero and 20% carbon dioxide levels, sample chamber 32 has a volume of 0.5 $mm^3$. For detecting component gases at lower concentrations, it may be necessary to increase the volume of sample chamber 32 correspondingly. Sample chamber assembly 22 may be made from a metal, such as aluminum, or a composite material, such as a polymer.

Source assembly 26 includes a source 36 and a reflector 38. Reflector 38 is made from aluminum and has a polished reflecting surface 40 that is either elliptical or parabolic in shape. Source 36 includes an infrared emitting element 42, which is supplied with an electrical current from electronic assembly 18 through electrical leads 44a and 44b. Emitting element 42 is positioned within chamber 46. Chamber 46 is surrounded by an envelope 48 made of a material that is a good transmitter of electromagnetic radiation in the infrared band of between 0.5 micrometers and 5.0 micrometers. Chamber 46 is void of any active gases which may react with the material of emitting element 42. In a preferred embodiment, chamber 46 is evacuated to form a vacuum. Envelope 48 must also be made from a material which is capable of being molded and which is gas impervious in order to avoid any exchange of atmospheric gas with chamber 46. In the illustrated embodiment, envelope 48 is made from quartz. Emitting element 42 is a filament of tungsten alloy. In the illustrated embodiment, source 36 is commercially available and. is marketed by Chicago Miniature under Model No. 7219. Chicago Miniature Model No. 7219 is marketed as a miniature panel light and is, therefore, commercially provided for the purposes of generating visible light. In the illustrated embodiment, source 36 is energized from a power source at a voltage level that is 50% of the rated voltage advised by Chicago Miniature Model No. 7219. Accordingly, in use, emitting element 42 gives off very little visible light. It emits primarily in the infrared region. Although, in the preferred embodiment, a commercially available miniature lamp is used, not all incandescent lamps are suitable. Incandescent lamps are typically enclosed with glass envelopes. Glass is a poor conductor of infrared radiation and, typically, cuts off transmission at wavelengths well below the infrared band.

Detector assembly 28 includes a 48-junction thermopile sensor 50 enclosed within an argon-filled container 52. Container 52 is closed by a sapphire window 54, which allows infrared radiation to penetrate the container. An optical filter 56 is positioned within container 52 in the radiation pathway between source 36 and sensor 50. Optical filter 56 passes energy at the wavelength of the absorption line of the component gas to be detected. In the illustrated embodiment, detector assembly 28 is commercially available and is marketed by Dexter Research under Model No. 2M. A plurality of leads 57 supply the output from sensor 50 to electronic assembly 18.

Detector assembly 28 is for the purpose of detecting a single component gas in a sample. Gas analyzer 15 may be adapted to detecting a plurality of component gases in a sample by utilizing a detector assembly 28' in which a plurality of sensors 50a, 50b and 50c are positioned within the radiation pathway. Each sensor 50a–50c is positioned behind an optical filter (not shown) having a transmission band at the absorption line of the component gas to be detected by the associated sensor 50a–50c. In detector assembly 28', a fourth sensor 50d is not exposed to the radiation from source 36 but is provided for the purpose of monitoring the temperature of the detector assembly for first-order temperature compensation of sensor outputs. If gas analyzer 15 is utilized to monitor the carbon dioxide level of a patient's respiration, or the carbon dioxide level within a biological test chamber, a single detector assembly 28 is provided wherein optical filter 56 transmits radiation at 4.25 micrometers. As previously set forth, concentration of carbon dioxide from between zero and 20% may be measured by a sample chamber volume of 0.5 milliliters. If gas analyzer 15 is utilized to measure automotive vehicle emission gases, a multiple sensor detector assembly 28' is utilized wherein the sensors 50a–50c are positioned behind optical filters which transmit at 3.5 micrometers for detecting hydrocarbons (hexane), 4.65 micrometers for detecting carbon monoxide and 4.25 micrometers for detecting carbon dioxide. Such a multiple sensor detector assembly 28' is commercially available and is marketed by Dexter Research under Model No. DR26 for dual sensor. A quad sensor, such as that illustrated in FIG. 10, is marketed by Armtec-Ragen under Model No. PS24.

In order to provide an accurate determination of the concentration of the component gas of interest in the sample, electronic assembly 18 amplifies the signal produced by sensor 50 by a factor of approximately 50,000 and provides first-order temperature compensation for ambient temperature. This latter function is necessary because a thermopile sensor drifts at a rate of 0.4% per degree centigrade. Electronic assembly 18 includes an amplifier 58 whose gain is established by a feedback resistor 60, connected between an output 62 and an inverting input 64, and by a resistor 65 connected between inverting input 64 and signal ground (FIG. 11). Sensor 50 is connected between a non-inverting input 66 of amplifier 58 and signal ground. The case 52 of detector assembly 28 is also grounded. Output 62 of amplifier 58 is supplied to the non-inverting input 68 of an amplifier 70. The gain of amplifier 70 is established by feedback resistors 72, 74 and $R_g$ and a resistor $R_1$ connected in series with an inverting input 76. Resistor $R_1$ is, in turn, connected with an output 78 of an amplifier 80. Amplifier 80 has a non-inverting input 82 connected to signal ground with a bias resistor 84. Amplifier 80 additionally includes an inverting input 86 connected to an output 91 of a temperature sensor 88 through a bias resistor 90. Temperature sensor 88 has an input that is connected with a source of voltage at 89. Inverting input 86 is additionally connected, through a bias resistor 96, with the wiper 95 of a potentiometer $R_z$ connected between a positive voltage source 92 and a negative voltage source 94. Amplifier 80 additionally includes a feedback resistor 98 connected between output 78 and inverting input 86.

Output 100 of amplifier 70 is supplied to an inverting input 102 of an amplifier 104. A non-inverting input 106 of amplifier 104 is supplied with a reference voltage produced by a unity gain amplifier 108 that is supplied with a stable voltage from a zener diode 110 connected in series with a bias resistor 112 to a voltage source 114. The reference voltage level on input 106 is adjustable by an adjustable resistor 117. The output of amplifier 104 provides a voltage $V_{out}$, which is proportional to the concentration of the detected component gas, at 120.

The value of $V_{out}$ on output 120 is as follows:

$$V_{out} = (V_{ref} - V_{det}) [1 + 2R_1/R_g] + V_{offset} + V_{tempcomp}$$

where $V_{ref}$ is the voltage at input 106;

$V_{det}$ is the voltage at output 62;

$R_1$ is the resistance of resistor $R_1$;

$R_g$ is the combined series resistance of resistors 72 and $R_g$;

$V_{offset}$ is the voltage at wiper 95; and $V_{tempcomp}$ is the voltage at output 91.

The span of amplifier chain in electronic assembly 18 is established by the $R_1/R_g$ term and is adjustable by adjusting the value of variable resistor $R_g$. The value of $V_{offset}$, which establishes the offset of the amplifier chain, is established by adjusting the position of wiper 95 of variable resistor $R_z$. Thus, it is seen that the amplifier chain in electronic assembly 18 allows for independent adjustment of the zero offset and the span. It is also seen that the temperature dependency of sensor 50 is compensated for by temperature sensor 88 and associated circuitry. Temperature sensor 88 detects ambient temperature. Because all components of gas analyzer 15 are encapsulated by encapsulation material 20, the temperature of sensor 50 is very stable and not susceptible to abrupt changes in ambient temperature. Furthermore, any changes in the temperature of sensor 50 are accurately detected by temperature sensor 88. As set forth above, temperature sensor 88 may be sensor 50d incorporated within detector assembly 28' behind a dark panel. Although the zero offset and the span of electronic package 18 are illustrated as being adjusted by adjustable resistors $R_z$ and $R_g$, such resistors could be replaced by interconnections with an automatic control system which could supply suitable calibration voltages to the amplifier chain of the electronic assembly according to known techniques, in order to avoid the necessity for manual calibration. Thus, it is seen that electronic assembly 18 is adaptable to stand-alone operation or to interface with an automatic control system.

In the illustrated embodiment, amplifier 58 is a chopper-stabilized amplifier, which is exceptionally stable. Such amplifier is commercially available from a variety of suppliers under industry Model No. LTC1050CS8. Amplifiers 70, 80, 104 and 108 are provided in a single package under Model No. LT1014DS. The positive and negative voltage sources may be supplied from a unipolar battery by the provision of a commercially available voltage converter (not shown). Emitting element 42 of source 36 is supplied continuously with a regulated DC voltage through lead 44a from a regulated DC voltage source 125. The opposite lead 44b is connected with signal ground. The voltage at voltage source 125 is six volts DC in the illustrated embodiment. Chicago Miniature panel light Model No. 7219 has a rated voltage of 12 volts DC.

Because emitting element 42 is positioned within a chamber that is void of reacting gases, there is no potential for the formation of oxides of the material composing the emitting element or of any surrounding material. Furthermore, because the emitting element is surrounded by a vacuum, in the preferred embodiment, its color temperature is maintained at a much lower wattage input because the emitting element is not being cooled by surrounding atmosphere. Also, the vacuum surrounding the emitting element significantly reduces variations in its color temperature due to ambient temperature variations. Additionally, because the emitting element is not heating the surrounding atmosphere, the detrimental effects of heating of surrounding components, resulting in second and third order errors, is virtually eliminated. Because oxidation of the emitting element does not occur, the radiation output of the element is exceptionally stable over very long periods of time. Because the source is inherently stable, there is no need for monitoring the temperature, or emissivity, of the source as an input to a stabilizing feedback control circuit, or as a compensation input to the detector amplifier circuitry, as required in prior infrared gas analyzers.

Because the source is inherently stable, there is, further, no necessity for interrupting the radiation beam between source 36 and sensor 50 to ensure a drift-free output level. Accordingly, the detrimental effects of prior art switched sources, in which system response time suffers from the relatively slow periodic cycling of the source, as well as the attendant reduction in system reliability from the thermal stress, are eliminated. The equally slow performance of the mechanically chopped systems, with the attendant reduction in system reliability from mechanical failures, are also eliminated.

The invention is capable of implementation in a system having exceptionally low noise levels and very stable, low drift, output. Importantly, the response time of the system, as defined as the time it takes to obtain a reading that swings from 10% to 90% of the span of the system, from a change of from zero gas to full scale gas at a flow rate of 250 milliliters per minute, may be reduced to below 200 milliseconds using the invention. This superior response time opens the possibility for real time monitoring of patient's respiration and the like. The compact package, within which the present invention may be embodied, opens up applications never before possible for infrared gas analysis technology. Portable hand-held engine analyzers may now be embellished with exhaust gas analysis capabilities. Such possibilities are, indeed, revolutionary.

Figure 12:
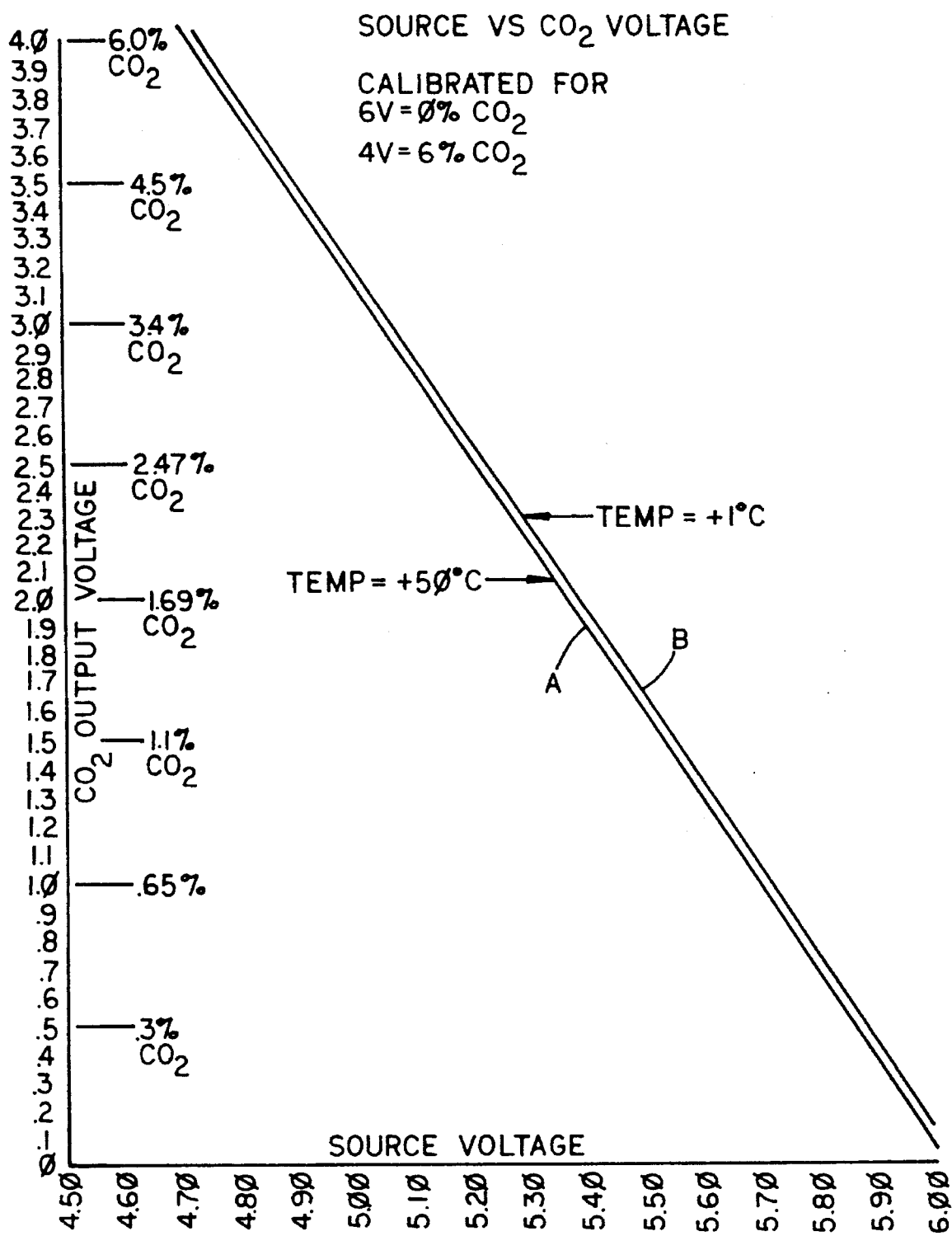
FIG. 12 is a graph comparing source input to voltage and detector output voltage.

The graph in FIG. 12 illustrates the relationship between the output voltage of detector, or sensor, 50 and the input voltage applied to source 36. An examination of FIG. 12 reveals that the graph of the detector output voltage for each value of source voltage is in the same proportion as the detector output for other source voltages. This is a linear relationship as depicted by sloping straight lines in FIG. 12. Because of the linear relationship between detector output voltage and source voltage, a simulation of an occlusion in the sample cell can be achieved by reducing the source voltage to a known level. Because of the linear relationship, the known reduced source voltage level should produce a known reduced output voltage level. The actual voltage on the detector output may be compared with the ideal reading in order to determine a calibration factor to be applied to actual detector output readings with a sample gas in the sample chamber.

By adjusting the source voltage to multiple different reduced known voltage levels within a range of concentrations of the component gas to be detected, a linearization of the instrument may be performed in an exceptionally fast, automated manner. The calibration factors obtained from such linearization may be either kept in a look-up table for use during gas sample measurements or may be used to generate the coefficients of a fourth order polynomial, as will be appreciated by the skilled artisan. Indeed, the present invention allows an almost infinite multiple point calibration/linearization of the gas analyzer.

Figure 13:
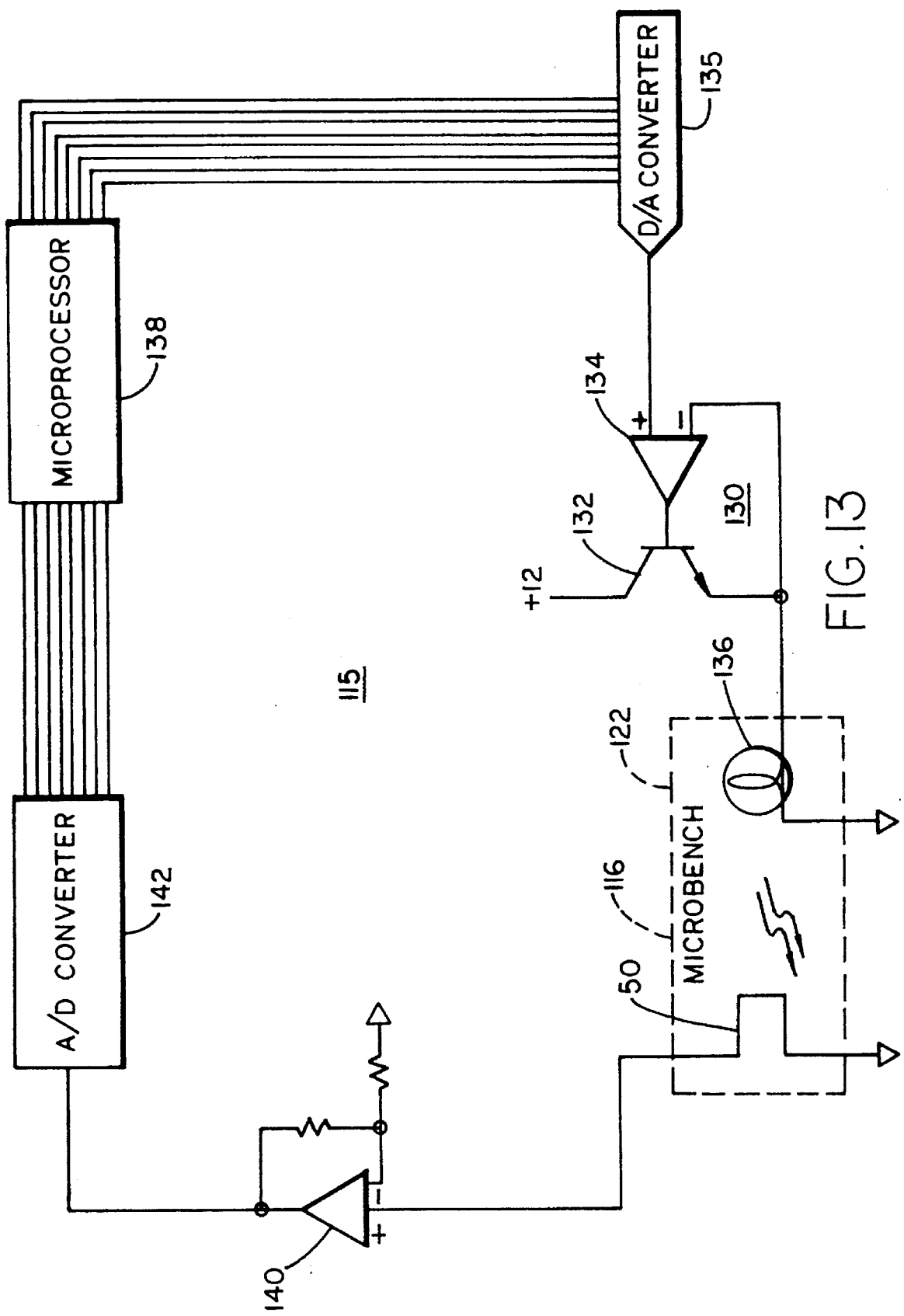
FIG. 13 is a block diagram of an alternative embodiment of an infrared gas analyzer according to the invention.

Such improved calibration technique may be implemented by an infrared gas analyzer 115 (FIG. 13). Gas analyzer 115 utilizes an infrared sensor assembly 116 having an infrared source 136 and detector 50. Infrared source 136 utilizes an emitter in an evacuated quartz envelope in the same manner as infrared emitting element 42. Source 136 is supplied electrical energy from a power supply 130. Power supply 130 is made up a transistor 132 whose collector is connected with a DC voltage source, such as 12 volts DC, and whose emitter is connected with a terminal of source 136. The base/emitter junction of transistor 132 is driven from the output of a unity gain amplifier 134. Unity gain amplifier 134 follows the output voltage level of a D/A converter 135. The analog output of D/A converter 135 is established by output levels of a microcomputer 138. The output of detector 50 is amplified by an amplifier 140 and supplied to the input of an A/D converter 142 whose digital output is supplied as an input to microcomputer 138.

In order to calibrate infrared gas analyzer 115, microprocessor 138 supplies a digital signal to D/A converter 135 that constitutes a reduced voltage level supplied to amplifier 134. Because transistor 132 is connected in an emitter-follower configuration, the voltage supplied to the emitting element of source 136 follows the output of D/A converter 135. The resulting output of detector assembly 128 is amplified by amplifier 140 and converted to digital form by A/D converter 142 and supplied as an input signal to microcomputer 138. Accordingly, a suitable program in microcomputer 138 allows the selection of one or more calibration levels for source 136 and the resulting output measured with a non-absorbing gas in the sensor assembly 116. The resulting calibration factor may then be stored within a look-up table in microcomputer 138.

Figure 14:
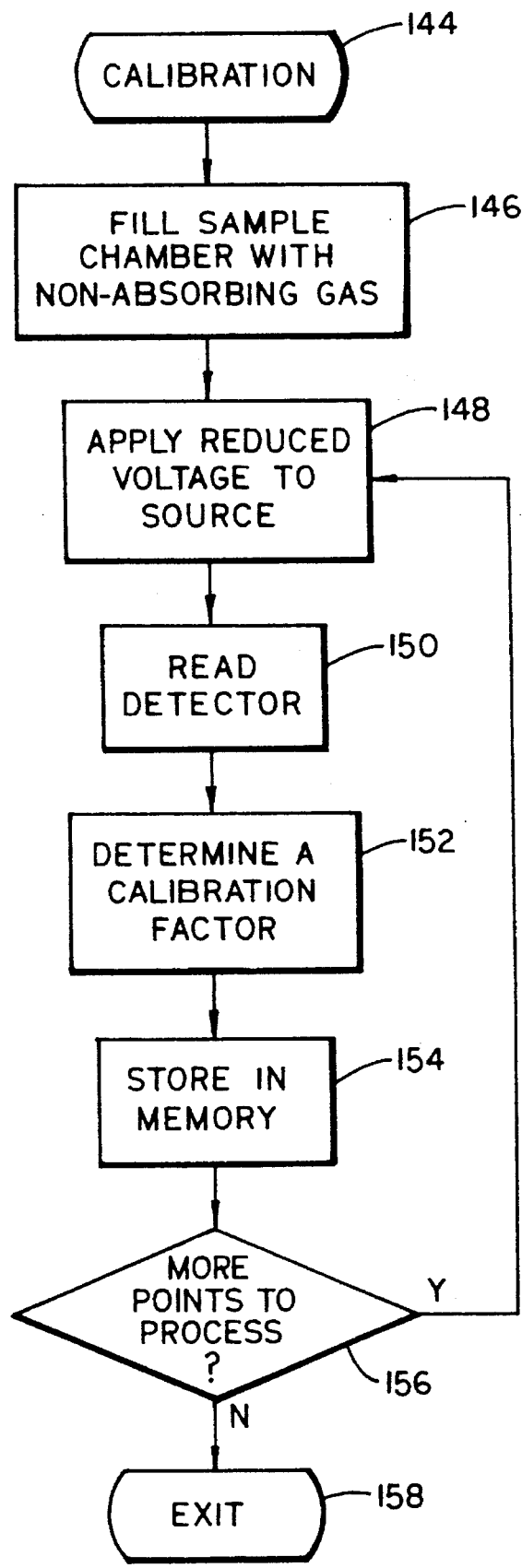
FIG. 14 is a flowchart of a control program for the infrared gas analyzer in FIG. 13.

When microcomputer 138 enters the calibration function 144, instructions are provided at 146 to a gas-handling subsystem (not shown) to fill the chamber assembly 122 of sensor assembly 116 with a gas that is non-absorbing at the absorption line of the gas to be detected by gas analyzer 115 (FIG. 14). With the non-absorbing gas in the sample chamber, microcomputer 138 applies at 148 a reduced voltage level to source 136. Detector 50 is read at 150 and microcomputer 138 determines a calibration factor 152, which is stored in memory at 154. It is then determined at 156 whether an additional calibration point is to be obtained. If so, the control returns to 148 where microcomputer 138 selects a new reduced voltage level to be applied to source 136. When all of the calibration points have been processed, as determined at 156, the calibration function is exited at 158.

Once a calibration table has been established in microcomputer 138, infrared gas analyzer 115 can then be utilized to measure the concentration of a component gas in a sample. If a gas handling subsystem (not shown) is utilized, microcomputer 138 causes the gas-handling system to fill sample chamber 122 with a sample gas. Alternatively, the sample gas may be supplied by diffusion to the sample chamber. With the sample gas in the sample chamber, microcomputer 138 supplies an output code to a D/A converter 135 to supply a full voltage level to source 136. The resulting level of radiation detected by detector 50 and supplied by A/D converter 142 to microcomputer 138 is applied to the look-up table in order to determine a concentration of the component gas in the gas sample. Microcomputer 138 may then produce a display, or the like, to indicate such concentration value.

Microcomputer 138 may operate source 136 with an unmodulated continuous voltage applied to the source in the same manner as gas analyzer 15. Alternatively, microcomputer 138 could apply a modulated voltage to source 136, for example, in the form of a square wave, in which source 126 is pulsed between alternating energized and non-energized periods. This latter form of modulated operation of source assembly 126 is capable of a somewhat more accurate gas concentration reading because a reference signal is developed. However, the response time of gas analyzer 115 would be commensurately slower than if the source 136 is not modulated.

Figure 15:
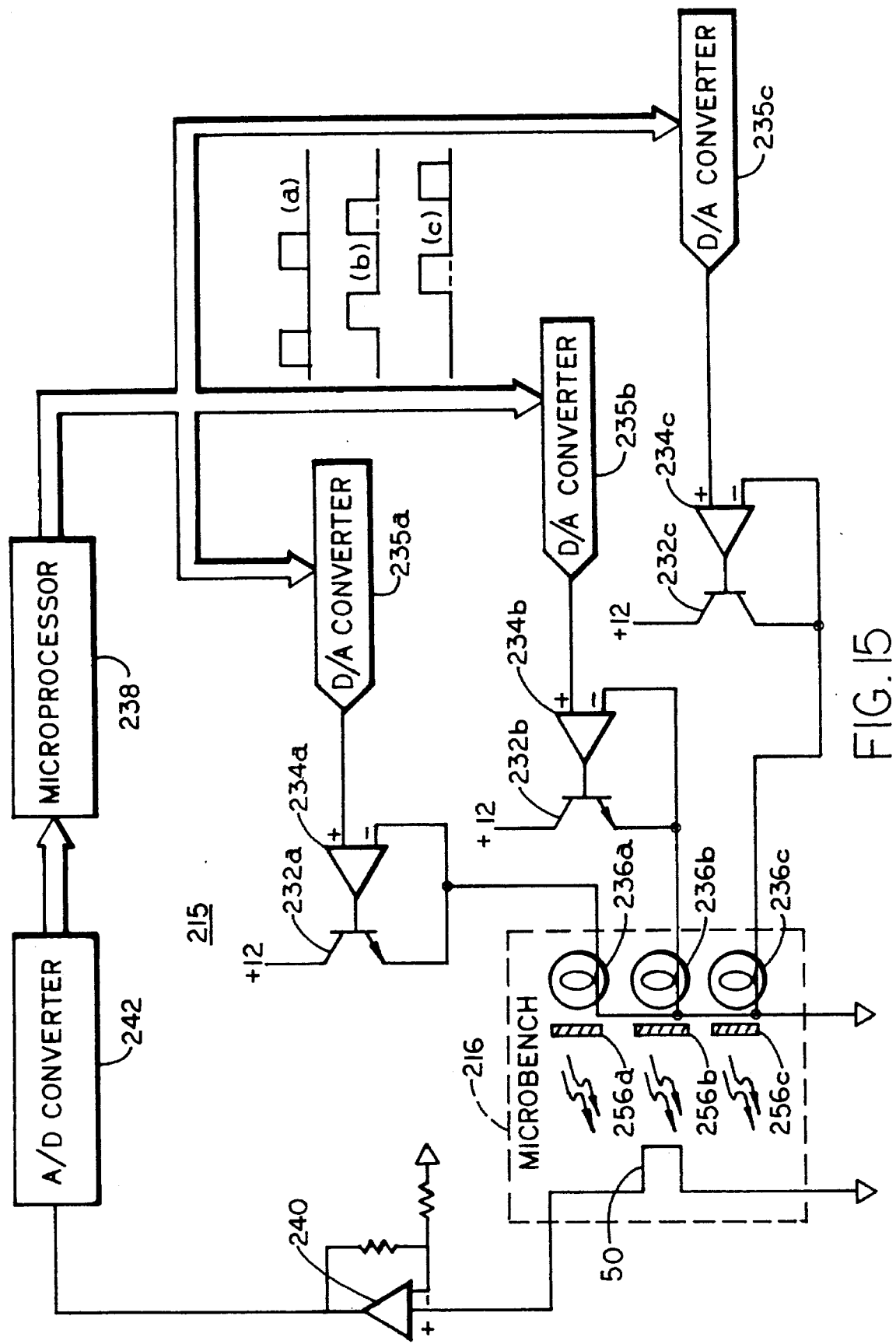
FIG. 15 is a block diagram of another alternative embodiment of the invention.

An example of an infrared gas analyzer 215 that is capable of detecting concentrations of multiple component gases in a sample is illustrated in FIG. 15. Gas analyzer 215 is useful, for example, in measuring multiple exhaust gases emitted from a vehicle engine. Gas analyzer 215 includes a sensor assembly 216 having a source assembly with three or more sources 236a, 236b, and 236c. Optical filters 256a, 256b, and 256c are each respectively positioned between one of the sources and a single detector 150. Each source 236a–236c is connected with the emitter of a transistor 232a–232c, respectively, which is driven in a collector-follower configuration by unity gain amplifiers 234a–234c. Amplifier 234a is driven by the output of a D/A converter 235a, which converts an output from a microcomputer 238 to a pulsed DC signal, as indicated in FIG. 15 at (a). Amplifier 234b is operated from the output of a D/A converter 235b, which is operated by microcomputer 238 to produce the waveform indicated at (b) in FIG. 15. Amplifier 234c is connected with the output of a D/A converter 235c, which is driven by microcomputer 238 to produce the waveform indicated at (c) in FIG. 15. Thus, it is seen that sources 236a, 236b, and 236c are each modulated and operated in a time-division multiplexed sequence. The radiation emitted by each of the sources is directed through its respective optical filters 256a–256c, each of which corresponds with an absorption line of one of the component-gases to be detected from a sample. The output of detector 50 is amplified by amplifier 240, converted to a digital format by A/D converter 242, and demultiplexed in microcomputer 238, in order to determine the concentrations of the component gases. Although gas analyzer 215 is illustrated with a single detector 50, separate detectors could be provided within sensor assembly 216 for each of the sources. However, analyzer 215 advantageously makes use of a single detector for detecting a plurality of component gas concentrations. In the illustrated embodiment, sources 236a, 236b, and 236c are modulated at a 0.33 hertz pulse repetition rate.

The infrared gas analyzer and method disclosed herein provides a calibration technique which is both accurate and capable of being implemented in an electronic control scheme. In FIG. 12, graph A illustrates a source/detector relationship at 50° C. Graph B illustrates the same relationship at 1° C. A comparison of these graphs A and B illustrate that the linearity is exceptionally immune to variations in ambient temperature. This may be explained, in part, by the vacuum surrounding the emitting element of the source. The vacuum resists the transmission of ambient temperatures to change the color temperature of the source. Because the source is relatively immune to variations in ambient temperature, and the detector is ambient temperature compensated, a calibration established at one ambient temperature will be valid at significantly different ambient temperatures. Importantly, the calibration technique disclosed herein is so readily performed upon the deployment of the instrument, that the instrument may be calibrated to the specific ambient temperature in which it is deemed operated. This results in yet further accuracy in the readings taken by the instrument.

Changes and modifications in the specifically described embodiments can be carried out without departing from the principles of the invention, which is intended to be limited only by the scope of the appended claims, as interpreted according to the principles of patent law including the Doctrine of Equivalents.

The embodiments of the invention in which an exclusive property or privilege is claimed are defined as follows:

1. An infrared gas analyzer for detecting a plurality of component gases in a sample, comprising:

a sample chamber having opposite ends thereof;

a source assembly having a plurality of infrared emitters at one of said opposite ends and at least one detector at the other of said opposite ends;

a plurality of filters in said sample chamber, each between one of said emitters and said at least one detector and passing radiation at an absorption line of one of the plurality of component gases;

a digital computer having at least one input port and at least one output port;

at least one digital-to-analog converter having a digital input connected with said at least one output port and having an analog output connected with at least one of said infrared emitters; and at least one analog-to-digital converter having an analog input connected with said at least one detector and a digital output connected with said at least one input port;

wherein said computer energizes said plurality of infrared emitters in time-division multiplexed sequence by supplying digital signals sequentially to said at least one digital-to-analog converter in order to sequentially energize said plurality of infrared emitters at energy levels determined by the values of said digital signals.

2. The infrared gas analyzer in claim 1 in which said detector output is a linear function of energy applied to each of said sources.

3. The infrared gas analyzer in claim 1 wherein said computer reduces the level of electrical energy applied to said infrared emitters, with a gas in said sample chamber that is non-absorbent of radiation at said absorption line of each of said plurality of gases, in order to determine a calibration factor for each of said plurality of gases.

4. The infrared gas analyzer in claim 1 wherein each of said plurality of filters correspond with an absorption line of an exhaust gas emitted from a vehicle engine.

5. The infrared gas analyzer in claim 1 wherein said at least one detector is a single detector.

6. The infrared gas analyzer in claim 1 wherein said at least one detector includes a separate detector for each of said plurality of infrared emitters.

7. The infrared gas analyzer in claim 1 wherein said at least one digital-to-analog converter includes a separate digital-to-analog converter for each of said plurality of infrared emitters.

* * * * *